United States Patent [19]
Edwards et al.

[11] Patent Number: 6,120,662
[45] Date of Patent: Sep. 19, 2000

[54] DEVICE FOR ELECTROCHEMICAL DETECTION OR MEASUREMENT

[75] Inventors: Stephen J. Edwards, Middlesex; Brian J. Birch, Chelveston; Barry G. Haggett, Luton Beds; John W. Dilleen, Seven Kings, all of United Kingdom

[73] Assignee: Eastman Kodak Company, Rochester, N.Y.

[21] Appl. No.: 09/061,655

[22] Filed: Apr. 17, 1998

[30] Foreign Application Priority Data

Apr. 29, 1997 [GB] United Kingdom .................. 9708587

[51] Int. Cl.⁷ .................................................. G01N 27/26
[52] U.S. Cl. ......................... 204/400; 204/409; 204/412; 204/434; 422/58; 422/66; 422/81; 422/100
[58] Field of Search ..................... 204/400, 409, 204/412, 415, 416, 418, 419, 431, 432; 422/58, 66, 81, 100; 436/66

[56] References Cited

U.S. PATENT DOCUMENTS

| | | |
|---|---|---|
| 3,607,079 | 9/1971 | Maxon et al. .............................. 422/66 |
| 3,926,765 | 12/1975 | Haddad .................................... 204/435 |
| 4,810,658 | 3/1989 | Shanks et al. . |
| 4,897,173 | 1/1990 | Nankai et al. ........................... 204/403 |
| 5,141,868 | 8/1992 | Shanks et al. . |
| 5,171,529 | 12/1992 | Schreiber .................................. 422/58 |
| 5,213,766 | 5/1993 | Flesher et al. ............................ 422/66 |
| 5,228,972 | 7/1993 | Osaka et al. ............................. 204/415 |
| 5,395,503 | 3/1995 | Parce et al. .............................. 204/409 |

FOREIGN PATENT DOCUMENTS

| | | |
|---|---|---|
| 0 170 375 | 2/1986 | European Pat. Off. . |
| 0 274 215 | 7/1988 | European Pat. Off. . |
| 0 399 227 A1 | 11/1990 | European Pat. Off. . |

*Primary Examiner*—T. Tung
*Attorney, Agent, or Firm*—Clyde E. Bailey, Sr.

[57] ABSTRACT

The device (1) has a cell (3) with an electrode structure for carrying out electrochemical detection or measurement of a liquid sample. A means for mechanically or pneumatically drawing the liquid sample into the cavity (20) of the cell (3) is provided. The drawing means may be in the form of a strip (10) which is mechanically drawn through the cell (3) drawing the liquid sample into the cavity (20) of the cell (3). The strip (10) can have a V-shape (44) portion which is placed in the liquid sample before the strip (10) is drawn through the cell (3).

5 Claims, 3 Drawing Sheets

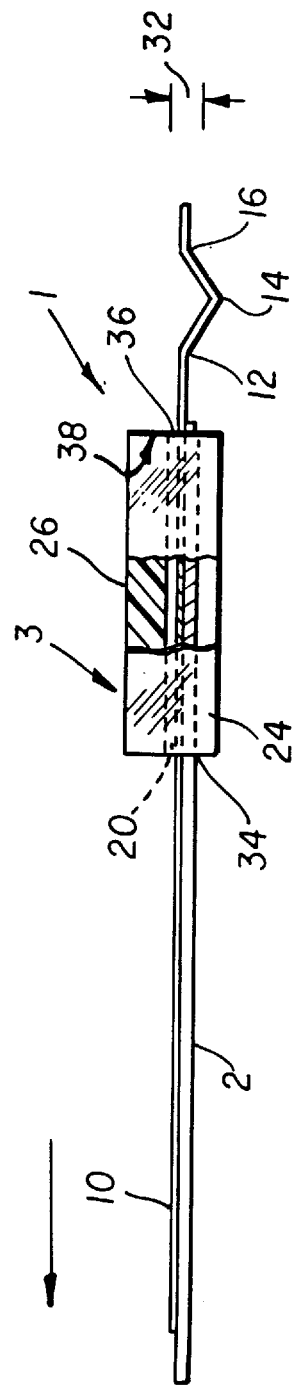
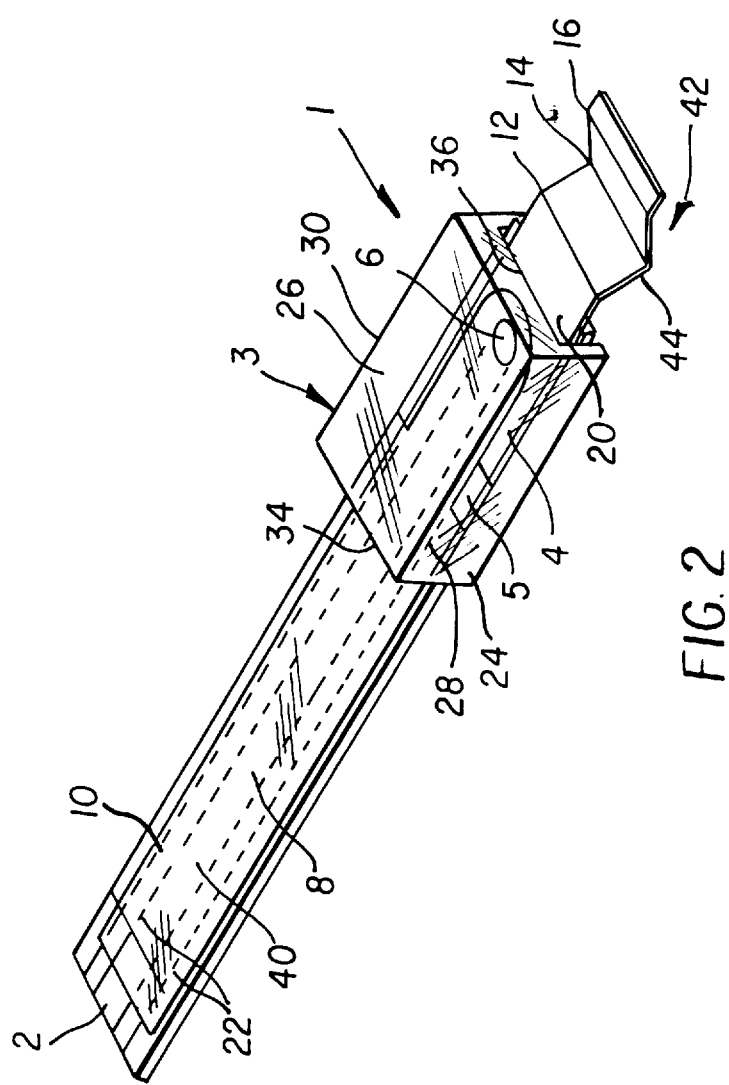
FIG. 1
FIG. 2

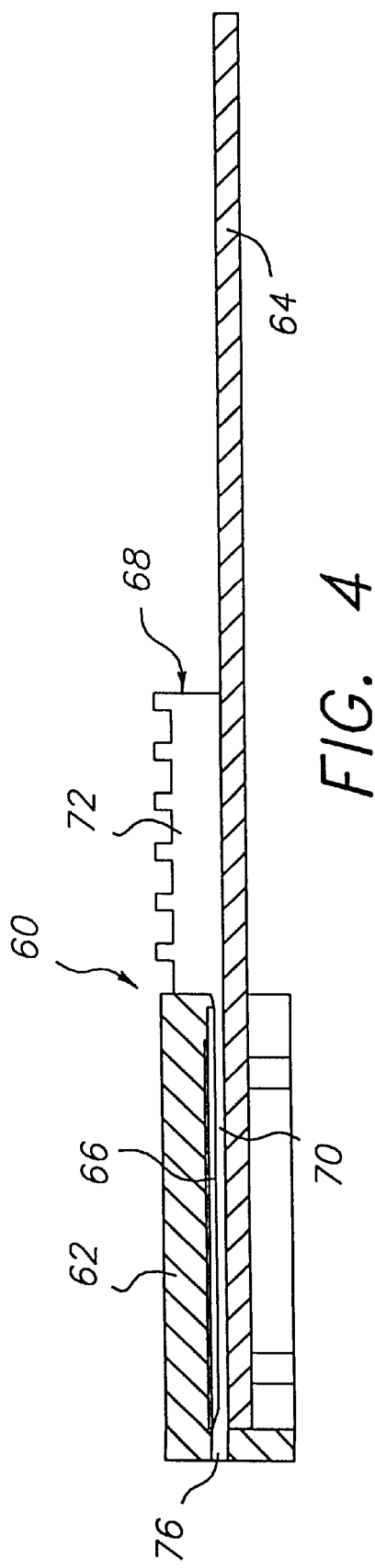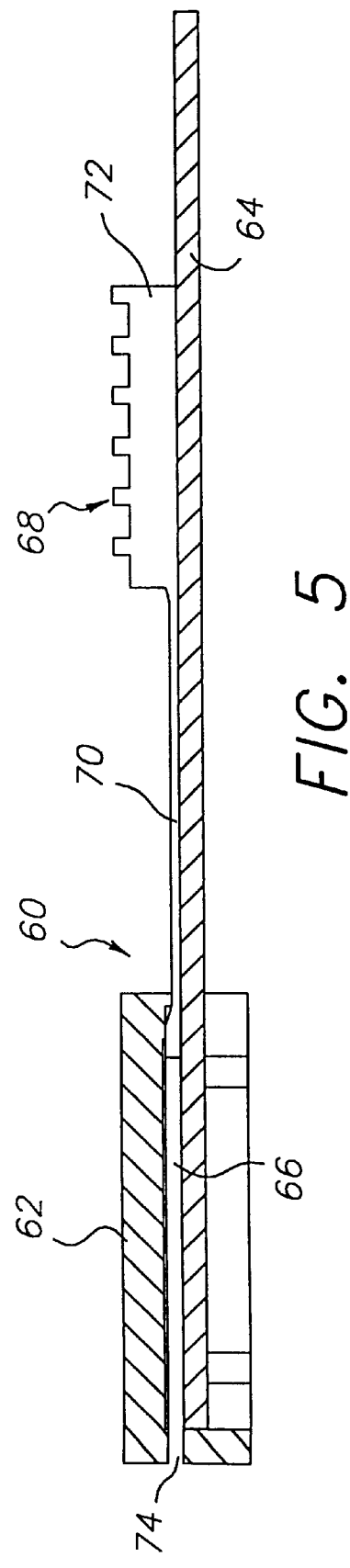

DEVICE FOR ELECTROCHEMICAL DETECTION OR MEASUREMENT

FELD OF THE INVENTION

This invention relates to a device for electrochemical detection or measurement particularly of a component of an aqueous or organic liquid sample.

BACKGROUND OF THE INVENTION

European patent no. EP-0170375 describes a sample collecting and testing device with a cavity which has dimensions small enough to enable the sample liquid to be drawn into the cavity by capillary action. Each cavity includes an electrode structure for making measurements of one or more electrically measurable characteristics of the sample.

Such capillary fill cells have the disadvantage of requiring the cell to have an exact depth which must be small enough to allow the capillary action. If the liquid sample is dirty or viscous, the contact angle between the cell and the liquid is destroyed and capillary action does not result. If the cell is immersed too far into the sample liquid, the sample can enter both ends of the cell and this can result in a bubble forming within the cell negating the measurement. Furthermore, for some forms of liquid sample, a surfactant is required to increase the capillary action.

SUMMARY OF THE INVENTION

According to the present invention there is provided a device for electrochemical detection or measurement comprising: a cavity for holding a liquid sample defined by two opposing plates; a planar electrode structure disposed on one of the plates within the cavity for detecting or measuring an electrically measurable characteristic of the liquid sample; and means for mechanically or pneumatically drawing the liquid sample into the cavity.

Preferably, the electrode structure comprises a reference electrode, a counter electrode and a working electrode. Preferably, there are also provided an insulating dielectric and a reagent in the cavity.

The means for mechanically or pneumatically drawing the liquid sample into the cavity may be in the form of a strip which can be drawn through the cell. Preferably, the strip is formed from an inert material.

Preferably, the strip extends through the cell and has a portion which extends out of the plane of the strip. Preferably, the portion is in the form of a V-shape.

The strip may be coated with a chemical coating, for example in the form of a reagent. There may be provided a protrusion from an internal surface of the cell which provides a scraping motion against the strip as the strip is drawn through the cell.

Preferably, the strip is extended to provide a protective casing around the cell.

As an alternative to the strip, the means for mechanically or pneumatically drawing the liquid sample into the cavity may be in the form of a means for reducing the pressure within the cavity. Preferably, the means for reducing the pressure within the cavity is in the form of a suction means such as a syringe.

BRIEF DESCRIPTION OF THE DRAWINGS

Embodiments of a device for electrochemical detection or measurement in accordance with the present invention is now described with reference to the accompanying drawings in which:

FIG. 1 is a side view of one embodiment of the device;

FIG. 2 is a perspective view of the device of FIG. 1;

FIG. 4 is a side section of another embodiment of the device in its empty state; and FIG. 5 shows the device of FIG. 4 in its filled state.

DETAILED DESCRIPTION OF THE INVENTION

Figure 3:
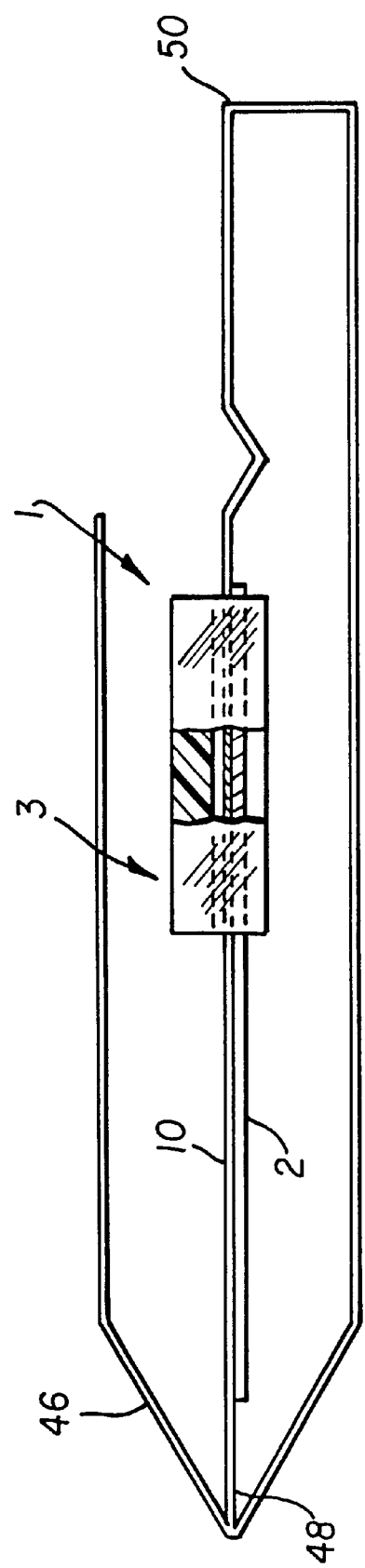
FIG. 3 is a side view of the device of FIGS. 1 and 2 with a protective casing.

Referring to FIGS. 1 to 3 of the drawings, there is provided a device (1) for electrochemical detection or measurement of a component of an aqueous or organic liquid sample.

The device (1) has a cell (3) in the form of an open ended cuboid structure having a base (24), a top (26) and two side walls (28), (30). The cell has a first open end (34) and an opposite second open end (36). The cell (3) defines a cavity (20) with a known volume. The internal height (32) of the cavity (20) between the base (24) and the top (26) of the cell (3) can be up to 3 mm high. The height (32) can be greater than 3 mm; however, a smaller height is preferable to avoid air bubbles forming within the cavity (20). Preferably, the height is approximately 0.5 to 1.0 mm.

The cell (3) is formed of a clear plastic material to provide visual verification that the liquid sample has been drawn through the cell (3) and that no bubbles are present within the cavity (20).

A plate (2) is provided on the base (24) of the cell (3) and the plate (2) extends outwardly from the cell (3) through the first open end (34) of the cell (3).

The portion of the plate (2) within the cavity (20) is printed with an electrode structure in the form of a plurality of electrodes (4, 5, 6) and a dielectric insulator (8). A layer of reagent is also provided. Electrode connectors (22) extend from the electrodes (4, 5, 6) within the cavity (20) along the portion of the plate (2) which extends out of the cell (3). The end of the plate (2) remote from the cell (3) can be attached to a remote analyzing means for taking the reading of the electrodes (4, 5, 6) during exposure to the liquid sample.

In an alternative arrangement, electrodes are disposed on opposite internal surfaces of the cell (3). This arrangement enables the size of the device (1) to be reduced.

A means for drawing a liquid sample into the cavity (20) is provided in the form of an inert strip (10) formed of a material which may be flexible such as cellulose acetate. The strip (10) is a flat elongate structure which has a width which is the same as the internal width of the cavity (20) and a height which is less than the height (32) of the cavity (20). The strip (10) extends through the cavity (20) such that a first portion (40) of the strip extends, before use, through the first open end (34) of the cell (3) in the same direction as the plate (2). A second portion (42) of the strip (10) extends, before use, from the second open end (36) of the cell (3).

The second portion (42) of the strip (10) which extends from the second open end (36) includes a portion of the strip (10) which is bent into the configuration of a V-shape (44). The second portion (42) of the strip (10) has a first bend (12) out of the plane of the strip (10), a second bend (14) which forms the apex of the V-shape and a third bend (16) which bends the strip (10) back into the plane of the strip (10). The strip (10) could be terminated at the point of the third bend (16). Alternative configurations of the strip (10) can also be used.

During the assembly of the device (1), the strip (10) is inserted into the cell (3) through the second open end (36)

such that the V-shape (44) does not need to enter the cell (3) until the device (1) is used.

The strip (10) can be coated in the vicinity of the V-shape (44) with a suitable releasable or immobilised reagent. A projection (38) may extend from the internal surface of the top (26) of the cell (3) to scrape the strip (10) as it is drawn through the cell (3).

The strip (10) could be formed with a protective casing (46) generally enclosing the device (1) as shown in FIG. 3. The casing (46) can protect the device (1) and be attached to the two ends (48, 50) of the strip (10). The casing (46) would be sufficiently large to enable the strip (10) to be drawn through the cell (3) without breaking the casing (46).

Before use, the end of the strip (10) with the V-shape (44) is in a position such that the V-shape (44) extends from the cell (3). To use the device (1), the V-shape (44) is placed into a liquid sample or the sample is placed on the V (44). The first portion (40) of the strip (10) which protrudes out of the first open end (34) of the cell (3), is pulled such that the V-shape (44) is drawn through the cell (3) in the direction of the arrow in FIG. 1. A drawing action impels a repeatable volume of the liquid sample into the cavity (20) of the cell (3). This provides a repeatable measurement of the liquid sample.

As the strip (10) is drawn through the cell (3), the projection (38) can scrape a surface of the strip (10) and release any reagent deposited on it. This can contribute to the subsequent reaction and measurement process.

The electrode structure is protected as it is disposed below level of the insulating dielectric (8) and thus the drawing action of the strip (10) into the cavity (20) will not harm the electrodes (4, 5, 6).

The strip (10) should be drawn completely through the cavity (20) to distribute the liquid sample over the entire surface of the plate (2) within the cavity (20).

It will be obvious to a person skilled in the art that the strip (10) can be formed of different materials and have different configurations and still achieve the same aim. It is possible that with certain liquid samples, the drawing of a planar strip will achieve the same drawing action of the liquid sample through the cavity.

In an alternative embodiment, the means of drawing the liquid sample into the cell is provided by suction. The device can incorporate a means for reducing the pressure of the air within the cavity of the cell when an opening to the cell is in contact with the liquid sample such that the liquid sample is drawn into the cavity. The liquid sample is held in the cavity by the surface tension of the liquid sample. The suction means can be in the form of a syringe attached to second opening in the cell.

Referring to FIGS. 4 and 5, a modified device 60 has a cover plate 62 mounted at one end of a rectangular substrate 64 to form a cell 66 therebetween. A strip 68 is slidably supported on the substrate 64 so as to dispose a channel part 70 within the cell 66 in its empty state (FIG. 4), and so as to be withdrawn by means of a gripping part 72 to fill the cell 66 (FIG. 5). The cell 66 has an opening 74 at one end that is sealed by a raised end wall 76 of the strip 68 in the empty state, further insertion of the strip 68 being arrested by abutment of its gripping part 72 with the cover 62. In operation, the device 60 in its empty state (FIG. 4) is positioned such that the closed cell opening 74 contacts the liquid to be sampled. The strip 68 is slid outwardly of the cell 66 until its movement is arrested by sealing abutment of a flank of the wall 76 with a rear projection of the cover 62 (FIG. 5). This movement draws a predetermined quantity of the liquid in to fill the cell 66, being held therein by suction, so that measurements can be carried out.

The cellulose acetate strip 10 of the first embodiment is convenient to manufacture and can be re-used. However, its inherent flexibility, especially when provided in exemplified 0.001 inch thickness, can make manufacturing to the required tolerances difficult for ensuring that all strips are of the same size, and thus that all samples of liquid are of the same volume. The strip 68 of the second embodiment is preferably made from a more rigid material, for example polyethylene, or more preferably, the more rigid high density polyethylene. Another suitable material is polymethylmethacrylate, although it is preferred that this material be used for the transparent cover 62. Such materials lend themselves to manufacture by injection moulding, which provides the necessary reproducibility. The substrate 64 may be formed from a ceramic material.

The forms of measurement which can be carried out using the electrode structure will be obvious to a person skilled in the art and a single example would be anodic stripping voltammetry of an organic or aqueous sample by a three electrode system for determining the amount of silver in a photographic fixer sample. A coating of ammonium thiocyanate could be used on the strip.

The invention has been described with reference to a preferred embodiment; However, it will be appreciated that variations and modifications can be effected by a person of ordinary skill in the art without departing from the scope of the invention.

What is claimed is:

1. A device for electrochemical detection or measurement comprising: a cavity for holding a liquid sample defined by two opposing plates; a planar electrode structure disposed on one of the plates within the cavity for detecting or measuring an electrically measurable characteristic of the liquid sample; and a flat, elongate inert strip containing a deposit of said liquid sample for drawing the liquid sample into and through the cavity thereby exposing said liquid sample to detection by said planar electrode structure disposed on said one of said plates, said strip being adapted to initially close a liquid entrance of the cavity, to be slidable through the cavity and to seal the cavity so as to retain the liquid sample by suction.

2. A device as claimed in claim 1, wherein the electrode structure comprises a reference electrode, a counter electrode and a working electrode.

3. A device as claimed in claim 1, wherein the flat, elongate inert strip extends through the cavity and has a portion which extends out of the plane of the strip.

4. A device as claimed in claim 1, wherein the flat, elongate inert strip is coated with a chemical coating comprising a reagent.

5. A device as claimed in claim 1, wherein means is provided inside the cavity for scraping the strip as the strip is drawn through the cavity.

* * * * *